United States Patent [19]

Porter et al.

[11] Patent Number: 4,704,295

[45] Date of Patent: Nov. 3, 1987

[54] ENTERIC FILM-COATING COMPOSITIONS

[75] Inventors: Stuart C. Porter, Hatfield; Edward J. Woznicki, Douglassville; Susan M. Grillo, North Wales; Louis F. D'Andrea, King of Prussia, all of Pa.

[73] Assignee: Colorcon, Inc., West Point, Pa.

[21] Appl. No.: 771,508

[22] Filed: Aug. 30, 1985

Related U.S. Application Data

[62] Division of Ser. No. 533,541, Sep. 19, 1983, Pat. No. 4,556,552.

[51] Int. Cl.[4] .......................... C08K 5/34; A61K 9/00; A61K 9/32
[52] U.S. Cl. ........................................ 427/3; 424/440; 424/482; 424/486; 424/497; 523/100; 524/89; 524/375
[58] Field of Search .................. 523/100; 524/89, 375; 424/32, 33, 440, 486, 497, 482; 427/3

[56] References Cited

U.S. PATENT DOCUMENTS 2,897,122  7/1959  Millar ................................ 424/33
2,993,837  7/1961  Millar et al. ...................... 424/33
4,543,370  9/1985  Porter et al. ..................... 523/100

OTHER PUBLICATIONS

Porter, "Aqueous Film Coating an Overview", *Pharmaceutical Technology*, Colorcon, Inc., 1980.

*Primary Examiner*—Herbert J. Lilling
*Attorney, Agent, or Firm*—John F. A. Earley; John F. A. Earley, III

[57] ABSTRACT

A non-toxic edible enteric film coating dry powder and aqueous enteric coating suspension for coating pharmaceutical tablets and the like; the enteric coated tablets; and methods of making the enteric coating dry powder, the aqueous coating suspension, and of coating the tablets.

25 Claims, No Drawings

ENTERIC FILM-COATING COMPOSITIONS

This is a divisional of co-pending application Ser. No. 533,541 filed on Sept. 19, 1983, now U.S. Pat. No. 4,556,552.

FIELD OF THE INVENTION

This invention relates to the field of aqueous enteric film-coating suspensions for coating pharmaceutical tablets and the like for preventing release of the ingredients of the coated tablet in the gastric juices of the stomach, and for releasing the ingredients in the intestines. It provides a non-toxic edible enteric film-coating dry powder for use in making an aqueous enteric coating suspension that may be used in coating pharmaceuticals with an intestinally soluble coating that is insoluble in the gastric juices of the stomach.

BACKGROUND OF THE INVENTION

Enteric coating solutions have been provided in the past, but have required the use of organic solvents. The organic solvents tend to pollute the atmosphere and present problems of safety and hygiene for workers, so it is necessary to take steps to prevent such pollution and this involves the use of expensive equipment. Also, organic solvents present a danger of fire or explosion, and expensive equipment is required to limit or reduce this danger.

Aqueous enteric coatings insoluble in gastric juices and soluble in the intestines have previously been proposed, but they have had problems including not providing sufficient protection against moisture penetration to the interior of the tablet. Also, tablets coated with such aqueous enteric coatings tend to disintegrate in the gastric juices of the stomach and to release their medicament prematurely into the stomach, rather than delaying tablet disintegration and release of ingredients until the tablet reaches the intestines as desired.

In Shinetsu U.S. Pat. No. 4,017,647, hydroxypropyl methyl cellulose phthalate, HPMCP, is dissolved in water and neutralized with a base and is applied to tablets by spray coating, but the coatings are not enteric until they undergo a subsequent acid treatment step.

J. W. Stafford, Sandoz AG, in *Drug Development and Industrial Pharmacy*, 8(4), 513–530 (1982), discloses a completely aqueous enteric film coating spray system with neutralized HPMCP for the enteric coating of tablets whereby 12.5% by wt. of HPMCP is dispersed in water and neutralized with base to make a spray solution, with the amount of base required per 100 g. HPMCP being 11.8 g. of 25% aqueous ammonia, 6.74 g. of NaOH (added dissolved in a little water for rapid dispersion), or 25.3 g. triethanolamine. The HPMCP is said to be usually dissolved after a few hours. Insoluble excipients such as talc and titanium dioxide are ball milled as aqueous dispersions before being added to the spray solution. The neutralized HPMCP film former is completely water soluble. To provide enteric protection, the neutralized HPMCP film on the tablet is converted to insoluble acid at the gastric juice pH, which is generally said to be about 1 to 3 pH.

Shinetsu Japanese Pat. No. 104,823/1981 discloses intestinally soluble protective coating agent composites for solid medicines characterized by dispersing a powdery intestinally soluble coating base agent having an average particle size of smaller than 100 microns in an aqueous medium containing a plasticizer sparingly soluble in water. It is advisable to add an appropriate dispersion aid or emulsifier to promote the dispersion or emulsion of the plasticizer. To prevent agglomeration of the coating dispersion, it is desirable to keep the temperature below 30° C. in the spray guns and pipes so as to avoid clogging of the pipes or spray gun nozzles.

Accordingly, it has been a problem to prevent the heat from jelling or coalescing the coating solution or dispersion in the spray equipment and causing the equipment to clog.

Japanese Pat. No. 104,823/1981 to Sekikawa et al. relates to intestinally soluble protective coating agent composites for solid medicines and teaches that the use of water soluble plasticizers destroys the enteric performance because such plasticizers are not resistant to gastric juices and do not prevent the tablet from disintegrating in the stomach.

Also, the Japanese patent discloses preparing a coating system by adding individual components: adding a wetting agent to water, dispersing a polymer into the water, adding a plasticizer, etc. The inventive system contemplates adding only one ingredient to water to make the coating dispersion, and that ingredient is the coating dry powder. However, the inventive dry powder system had to overcome problems of premature agglomeration and clogging in the spray apparatus. This problem was overcome by adding an ammonia solution after mixing and thoroughly wetting the coating dry powder particles in water.

SUMMARY OF THE INVENTION

The invention provides enteric film-coating compositions which overcome the problems of the prior art by providing a non-toxic edible enteric film-coating dry powder that is complete, and needs only to be dispersed in an aqueous solution to be ready for coating pharmaceutical tablets and the like. The film coating composition is shipped in dry powder form, with a saving in shipping cost because of its reduced weight since it is without the weight of any solvent.

The inventive film-coating enteric composition is stored in dry form which avoids problems of evaporation, attack by bacteria, and the deleterious effects of heat and/or cold on a liquid dispersion.

The non-toxic edible enteric film coating dry powder composition in accordance with the invention comprises a film-forming polymer, a plasticizer, an auxiliary film-forming polymer, pigment particles or substitute, and, optionally, an anti-caking agent. A coating suspension is made by mixing this dry powder into water and adding an anti-coalescing agent to prevent the coating suspension from clogging the nozzles and lines of the spray gun apparatus.

The polymer is polyvinylacetatephthalate, PVAP, having a phthayl content of about 55–62%, and having a particle size below 100 microns and preferably below 25 microns. The PVAP is about 70–85% by weight of the dry powder, and is preferably in the range of 75–80% by weight of the dry powder.

It is essential to use a water soluble plasticizer in the dry powder of the present invention. The water soluble plasticizer, when the dry powder is mixed into water, dissolves and becomes individual molecules which can react more efficiently with the PVAP particles suspended in the coating suspension to produce a more effective enteric coating when applied to tablets.

The auxiliary film-forming polymer is present in the dry powder to assist in the forming of a film on the tablets and also to act as a suspending agent for the polymer particles in the coating suspension. The preferred film-forming polymer is sodium alginate in an amount of up to 3% by weight of the dry powder and preferably in the range of 1–1.50% of the coating dry powder. Another auxiliary film-forming polymer which may be used is A4C, methyl cellulose made by Dow Chemical, which may be used up to 1.50% by weight of the dry powder and preferably in the range of 1–1.50% thereof. A medium viscosity grade sodium alginate is preferred.

The sodium alginate is a water soluble polymer which adds viscosity to the coating suspension, and also helps the coating adhere to the tablet surface while the PVAP particles are fusing to form a film. In other words, the sodium alginate makes the coating suspension thicker and thereby inhibits settlement and acts as a suspending agent, and also acts as a film former. Sodium alginate, although it is water soluble, is not soluble at low pH such as that found in gastric juices, and thus the sodium alginate does not interfere with enteric performance by disintegrating in the gastric juices of the stomach.

The sodium alginate acts as a suspension agent for the PVAP particles in the coating suspension. The sodium alginate also acts as a film former during the spraying operation to assist in providing an even coating on the tablets.

The pigment particles may be any of the pigments used in making coating dispersions for pharmaceutical tablets and the like. For example, the pigments may be FD&C and D&C Lakes, titanium dioxide, magnesium carbonate, talc, pyrogenic silica, iron oxides, channel black, and insoluble dyes. Also, natural pigments such as riboflavin, carmine 40, curcumin, and annatto. Other examples of suitable pigments are listed in Jeffries U.S. Pat. No. 31,49,040; Butler et al. U.S. Pat. No. 3,297,535; Colorcon U.S. Pat. No. 3,981,984; and Colorcon U.S. patent application Ser. No. 202,831, filed Nov. 6, 1980, now U.S. Pat. No. 4,543,370, by Porter and Woznicki; all of which are incorporated herein by reference.

The amount of pigment particles in the coating suspension presents a problem. If the coating suspension contains too much pigment, the pigment particles interfere with the polymer forming a film on the tablet. It has been found that adding more than about 15% pigment, by weight of the coating dry powder, interferes with the polymer forming a film on the tablet. Accordingly, if a light color is desired, a color that requires a 1 to 3 pigment to polymer ratio, mixing the pigments and polymer in that ratio to form the coating dry powder produces an eventual coating on the tablet that would not be acceptable. To overcome this problem, 10% titanium dioxide was mixed into the PVAP while it was being made. Then when the coating dry powder was being made, it was found that additional pigment particles up to 15% by weight of the coating dry powder could be mixed in with the titanized PVAP and other ingredients without interfering with the film forming of the coating suspension on the tablets. If a light color is not needed, the titanized PVAP need not be used.

With the non-titanized PVAP, up to about 15% pigment particles may be mixed into the coating dry powder without interfering with the forming of a film on the tablets. With the titanized PVAP, the titanium dioxide (10%) and other pigment particles (15%) may reach a total of 25% by weight of the coating dry powder without interfering with the forming of a film on the tablets.

The anti-caking agent may be Cab-O-Sil, fumed silica made by Cabot Inc., which is present preferably in the amount of about 1.00% of the coating dry powder. The fumed silica acts as a processing aid and also keeps the dry powder from lumping up while in storage. Use of the fumed silica is optional because any lumps that are formed can be screened out.

The anti-coalescing or stabilizing agent may be 30% ammonium hydroxide solution, $NH_4OH$, which may be used up to 8.00 milliliters per 100 grams of solids in the coating suspension, and preferably about 4.00 milliliters per 100 grams of solids. The ammonia is not a part of the coating powder; it is added after suspending the coating powder in water for about ½ hour, and before the spraying step. The coating suspension may be sprayed without adding the anti-coalescing agent, but there may be clogging problems if the spray equipment becomes too hot. If the anti-coalescing agent is added to the coating suspension, the coating suspension will not begin to coalesce and clog the spray apparatus until the temperature reaches about 60° C., whereas without the anti-coalescing agent the coating suspension may start to coalesce and clog the spray apparatus when the temperature reaches about 27°–30° C.

The inventive dry powder non-toxic enteric coating dry powder is made and sold by Colorcon, Inc., West Point, Pa. 19486, under the trademark COATERIC enteric film coating concentrate designed for use in an all aqueous system. The quality of the enteric properties of tablets coated by this aqueous system is equal to the quality of enteric film coatings made from an organic solvent system.

The method of applying the inventive enteric coating to tablets is as follows:

First, the ingredients of the coating dry powder are mixed together. Then the coating dry powder is dispersed into water to form a coating suspension, and an ammonia solution is added after the powder particles have been wetted out.

The coating dry powder is added slowly to the water with constant mixing. After about 30 to 40 minutes, the coating suspension is passed through a mesh screen and is then ready for use.

Certain tablet configurations or core compositions may require a precoat prior to the application of the inventive enteric suspension. Precoating with a water soluble polymer solution provides a smooth surface on an otherwise rough core. It also aids in preventing edge chipping and tablet abrasion.

To further illustrate the invention, the following examples are presented.

EXAMPLE 1

| A dry mix of | grams |
| --- | --- |
| Polyvinyl acetate phthalate (titanized) | 75.10 |
| Polyethylene glycol 3350 | 11.30 |
| Fumed silica | 1.00 |
| Sodium alginate | 1.50 |
| FD & C Yellow No. 6 Aluminum Lake | 5.05 |
| D & C Yellow No. 10 Aluminum Lake | 6.05 | is prepared by first blending the ingredients in a twin shell blender until uniform and then passing them though a Hammermill to disperse any small agglomerates.

Using a high speed agitator, 15 grams of the dry mix are suspended in 85 milliliters of deionized water. After stirring for ½ hour, 0.6 grams of concentrated ammonium hydroxide solution are added to the suspension. After 5 minutes of additional stirring, the coating suspension is ready for application to tablets.

EXAMPLE 2

A dry mix is made in accordance with Example 1 except that 10 grams of polyethylene glycol 3350 are used instead of 11.30 grams.

EXAMPLE 3

A dry mix is made in accordance with Example 1 except that 20 grams of polyethylene glycol 3350 are used instead of 11.30 grams.

EXAMPLE 4

A dry mix is made in accordance with Example 1 except that 10 grams of polyethylene glycol 8000 are substituted for the polyethylene glycol 3350.

EXAMPLE 5

A dry mix is made in accordance with Example 1 except that 17 grams of polyethylene glycol 8000 are substituted for the polyethylene glycol 3350.

EXAMPLE 6

A dry mix is made in accordance with Example 1 except that 0.5 grams of fumed silica are used instead of 1.00 gram.

EXAMPLE 7

A dry mix is made in accordance with Example 1 except that 1.5 grams of fumed silica are used instead of 1.00 gram.

EXAMPLE 8

A dry mix is made in accordance with Example 1 except that 1.00 gram of sodium alginate is used instead of 1.50 grams.

EXAMPLE 9

A dry mix is made in accordance with Example 1 except that 3.00 grams of sodium alginate are used instead of 1.50 grams.

EXAMPLE 10

A dry mix is made in accordance with Example 1 except that 70.00 grams of polyvinyl acetate phthalate are used instead of 75.10 grams.

EXAMPLE 11

A dry mix is made in accordance with Example 1 except that 85.00 grams of polyvinyl acetate phthalate are used instead of 75.10 grams.

EXAMPLE 12

A dry mix is made in accordance with Example 1 except that 1.00 gram of methyl cellulose is substituted for sodium alginate.

EXAMPLE 13

A dry mix is made in accordance with Example 1 except that 1.50 grams of methyl cellulose are substitued for the sodium alginate.

EXAMPLE 14

| A dry mix of | grams |
|---|---|
| Polyvinyl acetate phthalate | 85.00 |
| Polyethylene glycol 3350 | 12.00 |
| Fumed silica | 1.30 |
| Sodium alginate | 1.70 |
| Aluminum hydrate | 11.10 |

The ingredients are mixed in accordance with the method of Example 1 to produce a clear film coating.

EXAMPLE 15

| A dry mix of | grams |
|---|---|
| Polyvinyl acetate phthalate | 72.50 |
| Polyethylene glycol 3350 | 10.00 |
| Sodium alginate | 1.50 |
| FD & C Yellow No. 6 Aluminum Lake | 10.00 |
| Titanium dioxide | 5.00 |

The ingredients are mixed in accordance with the method of Example 1.

Performance of the Inventive Enteric Coating Suspension

A modified U.S.P. enteric test was used to assess the enteric efficiency of aspirin (500 mg.) tablets coated with the inventive enteric coating composition (approximately 6.5% w/w coating applied). 150 tablets were examined in a modified disintegration tester for 4 hours, using 0.1 N HCl as the test medium at 37° C. Subsequently, the disintegration time in buffer pH=6.8 was also evaluated.

Results indicated an ability to resist breakdown in gastric juice for the prescribed period, while disintegration time in the buffer solution was 9-12 minutes (the time being 1-2 minutes for uncoated cores).

In the evaluation in simulated gastric juice, some slight softening of the coating was observed, so an evaluation of the release of aspirin in this medium over an 8-hour period was carried out using U.S.P. dissolution apparatus (paddle method-100 rpm). A comparison was made with some commercially available brands of enteric coated aspirin tablets which had been coated using organic solvent and results indicated that in all cases a maximum of only 1-2 mg (which equals about 0.1 to 0.3%) of aspirin was released through the coatings in this period, and this is satisfactory.

A test of aspirin tablets coated with the inventive enteric coating showed that the coating resists simulated gastric juices for a period of 4 hours with only a 1% penetration of aspirin through the coating.

An enteric coating comprises, typically, 5-10% of the weight of the tablet, in order to get the enteric result, depending on the size, weight, and shape of the tablet. A small tablet requires a larger percentage of weight of the tablet for enteric coating than does a larger tablet.

For a clear film coating, without pigments, the dry powder coating composition includes aluminum hydrate, the colorless carrier of the dye which together forms an aluminum lake, and the aluminum hydrate simulates the presence of a lake pigment, and prevents the gel temperature of the clear coating suspension from dropping to below 35° C. It has been found that without the color pigments in the coating suspension, the gel temperature of the coating composition falls to about 35° C. which might result in clogging of the spray apparatus. At least about 4% of the enteric dry powder should be pigment particles, or clear particles such as aluminum hydroxide, to avoid the clogging problem, and preferably the percentage should be 7.50% and above. Accordingly, to solve this problem, the aluminum hydrate is substituted for the absent color lake pigments.

Tablets coated with the inventive coating dispersion have an intestinally soluble coating.

The sodium alginate makes the inventive coating suspension a thicker suspension. It acts as a suspending agent to prevent settlement of the solid material including the polymer, and it also acts as a film former. In the early stages of the coating process, the inventive coating suspension is forming a film by using the 20% dissolved polymer that is coming out of solution. The polymer is essentially insoluble in water and about 80% of it is in suspension. Discrete particles of polymer have to soften and are softened by the aid of the temperature in the process and by the presence of the plasticizer. This process of coating is different from coating with a polymer that is dissolved in solvent and must come out of solution to form a film on a tablet. The presence of the alginate in the inventive coating suspension gives the film some sort of integrity in its early stages. The alginate helps the film particles to adhere to the tablet while the fusion process is taking place. So the alginate serves two purposes, as a suspension agent, and as a film formation aid.

It has previously been suggested to use chilled water in preparing aqueous enteric coating suspensions. But even keeping the water at 10°-20° C. while preparing the coating suspension, the risk of premature agglomeration of the polymer, which clogs up the lines and spray nozzles, is still present, particularly when coating tablets on a production scale. When this happens, the spray nozzle blocks up, the coating suspension backs up through the feed lines to the pump, and everything gets clogged up with polymer. Agglomeration and fusion of particles of polymer occurs at below 35° C., about 27°-30° C., if the coating suspension does not contain pigments or ammonium hydroxide. This does not happen in organic solvent coating solutions because the polymer particles are in solution, instead of suspension.

By adding surfactants to an aqueous coating suspension, it is possible to increase the coalescing temperature a few degrees, but not enough to guarantee blockage-free spray film coating. However, the addition of an alkali, preferably ammonium hydroxide 30% solution in water, to the coating suspension in an amount of up to 8.00 milliliters of ammonium hydroxide for every 100 grams of dry powder, significantly elevates the temperature at which agglomeration occurs to in excess of 60° C., a safety margin of at least 30° C. This quantity of ammonium hydroxide solution which raises the agglomeration or gel temperature to about 60° C. is not sufficient to completely dissolve all of the polymer particles, but instead dissolves only about 20% of the PVAP particles. This 20% of PVAP particles in sblution acts as a protective colloid on the undissolved PVAP particles to prevent coalescing and blockage of the spray lines and guns, and also avoids the tacky coating which would be produced by having too much PVAP in solution. This 20% quantity of PVAP particles in solution also insures good enteric properties of the coating without it swelling in the gastric juices or rupturing in the stomach. The more PVAP that is put into solution, the higher the coalescing temperature becomes, but a high percentage of dissolved PVAP can create other problems. So only a portion of the PVAP is dissolved in the coating suspension, in the range of about 20-40% of the PVAP.

The addition of the ammonium hydroxide solution to the coating suspension is preferably in the range of about 8.00 milliliters to 4.00 milliliters per 100 grams of solids in the coating suspension. Above 8.00 milliliters of the ammonium hydroxide solution, the coating starts to get tacky, and below about 4.00 milliliters, the gel temperature of the coating composition is not elevated enough to insure the avoiding of clogging of the spray apparatus. The addtion of 2.00 milliliters of ammonium hydroxide solution per 100 grams of coating powder improves the coalescing temperature, to about 35°-40° C., but it does not give the 30° C. safety buffer that is provided by adding 4.00 milliliters of ammonium hydroxide solution which provides a coalescing temperature of about 60° C.

Instead of adding ammonium hydroxide solution to the coating suspension, a stable alkali may be added to the coating dry powder such as sodium carbonate or sodium bicarbonate in an amount equivalent to the addition of the ammonium hydroxide solution. However, there may be some caking of the coating dry powder in storage; the gel temperature of the coating suspension may not be as high as the gel temperature of the coating suspension formed with ammonium hydroxide solution; and the resulting coating may not be as good an enteric coating.

The word "pigment" as used herein in the specification and claims includes clear "pigments" such as aluminum hydroxide which may be substituted for FD&C lakes to make a clear coating powder and a clear enteric coating suspension.

An advantage of the inventive enteric coating powder is that it is shipped to the customer who adds only water and ammonia to the powder to form an enteric coating suspension. No longer does the customer have to form a polymer solution into which he must mix a pigment dispersion. The enteric film-coating suspension is made in just one mixing operation.

We claim:

1. A non-toxic edible enteric film coating dry powder for use in making an aqueous enteric coating suspension which may be used in coating pharmaceutical tablets and the like, comprising a dry mixture including powdered particles of an edible non-toxic film-forming polymer of micronized polyvinylacetate-phthalate, PVAP, an edible water-soluble plasticizer for said polymer, an auxiliary film-forming suspending polymeric agent for the PVAP, and pigment particles.

2. The enteric coating dry powder of claim 1, wherein the edible polymer plasticizer is a solid polyethylene glycol plasticizer.

3. The enteric coating dry powder of claim 1, wherein the edible polymer plasticizer is polyethylene glycol 3350 or 8000.

4. The enteric coating dry powder of claim 1, including fumed silica.

5. The enteric coating dry powder of claim 1, the PVAP being titanized PVAP containing up to 10% titanium dioxide by weight of the coating dry powder.

6. The enteric coating dry powder of claim 5, said pigment particles being FD&C and D&C lakes, titanium dioxide, magnesium carbonate, talc, pyrogenic silica, iron oxides, channel black, riboflavin, carmine 40, curcumin, annatto, or insoluble dyes.

7. The enteric coating dry powder of claim 1, said pigment particles being aluminum hydroxide.

8. The enteric coating dry powder of claim 1, wherein by weight
the PVAP is 75.10 parts,
the plasticizer is 11.30 parts,
the auxiliary film-forming polymer is 1.50 parts,
and the pigment is 11.10 parts,
of the mixture.

9. The enteric coating dry powder of claim 8, wherein by weight
the PVAP is 70 to 85 parts,
the plasticizer is up to 20 parts,
the auxiliary film-forming polymer is up to 3 parts,
and the pigment is up to 25 parts,
of the mixture.

10. The enteric coating dry powder of claim 1, wherein by weight
the PVAP is 75 to 80 parts,
the plasticizer is 10-17 parts,
the auxiliary film-forming polymer is 1.0-1.5 parts,
and the pigment is 4 to 20 parts,
of the mixture.

11. The enteric coating dry powder of claim 1, wherein
the PVAP particles are below 100 microns in size.

12. The enteric coating dry powder of claim 1, wherein
70-85% of PVAP particles are below 25 microns in size.

13. The enteric coating dry powder of claim 1, wherein
75-80% of the PVAP particles are below 25 microns in size.

14. An enteric coating suspension comprising
micronized PVAP particles,
edible water-soluble plasticizer,
an auxiliary film-forming polymer,
pigment particles,
an ammonium hydroxide solution,
and water.

15. The enteric coating suspension of claim 14, including
fumed silica.

16. The enteric coating suspension of claim 14, wherein by weight
the PVAP is 70 to 85 parts,
the plasticizer is up to 20 parts,
the auxiliary polymer is up to 3 parts,
the pigment is up to 25 parts,
and the ammonium hydroxide solution is up to 8 parts per 100 parts of solids in the suspension.

17. The enteric coating suspension of claim 14, wherein
about 20% of the PVAP is in solution.

18. The enteric coating suspension of claim 15, wherein by weight
the PVAP is 75-80 parts,
the plasticizer is 10-17 parts,
the auxiliary polymer is 1.0-1.5 parts,
the pigment is 4 to 20 parts,
the ammonium hydroxide solution is 4 parts per 100 parts of solids in the suspension,
and the fumed silica is 1 part.

19. In an aqueous coating system, a method comprising the steps of
micronizing particles of PVAP,
and mixing the PVAP particles with particles of an edible water-soluble plasticizer, an auxiliary film-forming suspending polymeric agent for the PVAP, and pigment particles, to form an enteric dry powder.

20. In an aqueous coating system, a method comprising the steps of
micronizing particles of PVAP,
and mixing the PVAP particles with particles of an edible water-soluble plasticizer, an auxiliary film-forming polymer, and pigment particles, to form an enteric dry powder, including
mixing the enteric dry powder into water,
and after the powder particles are thoroughly wetted, adding an ammonium hydroxide solution to form an enteric coating suspension.

21. The method of claim 20, including
spraying the enteric coating suspension onto tablets to form an enteric coating thereon.

22. An enteric costing suspension comprising
micronized PVAP particles,
edible water-soluble plasticizer,
an auxiliary film-forming polymer,
pigment particles,
fumed silica,
an ammonium hydroxide solution,
and water,
about 20% of the PVAP being in solution,
wherein by weight the PVAP is 75-80 parts,
the plasitcizer is 10-17 parts,
the auxiliary polymer is 1.0-1.5 parts,
the pigment is 4 to 20 parts,
the ammonium hydroxide solution is 4 parts per 100 parts of solids in the suspension,
and the fumed silica is 1 part.

23. A method of coating tablets with an aqueous coating system comprising the steps of
micronizing particles of PVAP,
mixing the PVAP particles with particles of an edible water-soluble plasticizer, an auxiliary film-forming polymer, pigment particles, and fumed silica, to form an enteric dry powder,
the PVAP being 70 to 85 parts,
the plasticizer being up to 20 parts,
the auxiliary polymer being up to 3 parts,
the pigment being up to 25 parts,
mixing the enteric dry powder into water,
and after the powder particles are thoroughly wetted, adding an ammonium hydroxide solution to form an enteric coating suspension,
and spraying the enteric coating suspension onto tablets to form an enteric coating thereon.

24. The enteric coating dry powder of claim 1, wherein
the auxiliary film-forming polymer is sodium alginate or methyl cellulose.

25. The method of claim 19, wherein
the auxiliary film-forming polymer is sodium alginate or methyl cellulose.

* * * * *